United States Patent [19]
Preidel et al.

[11] Patent Number: 4,919,770
[45] Date of Patent: Apr. 24, 1990

[54] METHOD FOR DETERMINING THE CONCENTRATION OF ELECTRO-CHEMICALLY CONVERTIBLE SUBSTANCES

[75] Inventors: Walter Preidel, Erlangen; Konrad Mund, Uttenreuth, both of Fed. Rep. of Germany

[73] Assignee: Siemens Aktiengesellschaft, Berlin and Munich, Fed. Rep. of Germany

[21] Appl. No.: 945,065

[22] Filed: Dec. 19, 1986

Related U.S. Application Data

[63] Continuation of Ser. No. 515,759, Jul. 21, 1983, abandoned.

[30] Foreign Application Priority Data

Jul. 30, 1982 [DE] Fed. Rep. of Germany ....... 3228542

[51] Int. Cl.$^5$ ............................................. G01N 27/52
[52] U.S. Cl. .................................. 204/153.1; 204/403; 128/635
[58] Field of Search ............... 204/1 T, 1 P, 1 K, 1 Y, 204/1 B, 406, 403, 415; 128/635

[56] References Cited

U.S. PATENT DOCUMENTS 4,340,458  7/1982  Lerner et al. ...................... 204/1 T
4,366,033  12/1982  Richter et al. ...................... 204/1 T

OTHER PUBLICATIONS

Bard et al., "Electrochem. Methods Fund. and Appl.", NY, J. Wiley & Son, 1980, Chapter 9, pp. 316–397.

Primary Examiner—Nam X. Nguyen
Attorney, Agent, or Firm—Mark H. Jay

[57] ABSTRACT

The invention involves a method for determining the concentration of electro-chemically convertible substances in a solution by means of an analyzer equipped with a test electrode, so that a precise determination of the concentration, dependable over extended periods, is possible. The invention provides for a potential varying with time within a potential interval to be impressed on the test electrode, for an ac voltage of a predetermined amplitude and frequency to be superimposed on this potential, and for the real and/or imaginary portions of the impedance to be determined for at least one potential step, thus determining the concentration. The method is particularly suited for determining the concentration of glucose in body fluids.

1 Claim, 1 Drawing Sheet

METHOD FOR DETERMINING THE CONCENTRATION OF ELECTRO-CHEMICALLY CONVERTIBLE SUBSTANCES

This is a continuation of application Ser. No. 515,759 filed July 21, 1983, abandoned.

BACKGROUND OF THE INVENTION

The invention relates to a method of determining the concentration of electro-chemically convertible substances in a solution by, means of an analyzer which includes a test electrode.

Determining the concentration of dissolved substances, particularly in the presence of foreign substances causing interference, is important in many fields. A representative example of this is the determination of glucose in body fluids such as blood. Such a determination is especially necessary for diabetics.

Diabetic therapy can be greatly improved if patients are continuously, i.e., at a constant basal rate, supplied with insulin, and if additional doses of insulin are called for before meals. In keeping with this principle, implantable pumps which are connected to a container filled with a supply of insulin have already been developed. The pumps are operated by a programmable control unit. However, the objective here is a closed control system which requires a sensor for determining the concentration of glucose in the patient's blood.

Implantable electro-catalytic sugar sensors for determining the concentration of glucose are already in existence. Such sensors have a test electrode, of platinum for example, which is located in front of a membrane which is placed so that it determines the rate of diffusion (see U.S. Pat. No. 4,366,033). In order to determine the concentration of glucose, a potential profile is impressed on the test electrode using a potentiostat, whereby two levels are specified: a positive and a negative potential. In the case of the positive potential, the test electrode is regenerated; i.e., the reaction products on the electrode are oxidized. If the test electrode reaches the negative potential the current is integrated. The charge determined here is the test signal which is allocated to the glucose concentration. However, in the case of the implantable electro-catalytic glucose sensors, difficulties arise in suppressing the influence of interfering factors such as urea and amino acids which are components of the body fluid.

SUMMARY OF THE INVENTION

The object of the invention is a method for determining the concentration of electro-chemically convertible substances in a solution using an analyzer equipped with a test electrode, so that a precise determination of the concentration, which is dependable over an extended period even in the presence of other reactants, can be obtained.

The invention achieves this objective by impressing a time-variant potential on the test electrode within a potential interval, by superimposing an ac voltage of a predetermined amplitude and frequenccy on this potential, and by determining the real and/or imaginary portion of the impedance for at least one potential step, and from this, the concentration.

When the invention is used, the preferred procedure is for the real and imaginary portions of the impedance to be determined for several potential steps.

To obtain a large amount of information when the method is used, an ac voltage is superimposed on the dc voltage and the "response" of the actuated electrochemical system is analyzed. The resulting measured value is the impedance in the form of is real and imaginary portions; i.e., as a function of the ac voltage frequency and the potential. This makes it possible to measure a potential-dependent impedance spectrum of the electro-chemical reaction and, for example, characterize the electrical quantities as an equivalent circuit for this reaction.

The invention is particularly suited for determining the concentration of glucose, urea, and amino acids in fluids, such as body fluids. In the case of amino acids, the total concentration is determined. When physiological solutions are examined, it is also possible to determine the concentration of the above-mentioned substances in parallel (simultaneously). Furthermore, the invention is also useful for determining the concentration of gases dissolved in fluids, such as oxygen and chlorine.

In general, the invention features an improved method for determining the concentration of electrochemically convertible substances in a solution by means of an analyzer using a test electrode, in which the improvement comprises impressing a potential varying with time within a potential interval on the test electrode, superimposing an ac voltage with a predetermined amplitude and frequency on this potential, establishing the real and/or imaginary portion of the impedance for at least one potential step, and determining the concentration from the impedance.

In preferred embodiments, the improvement is characterized by the fact that the real and the imaginary portions of impedance are determined during several potential steps; an ac voltage of different frequencies is superimposed on the potential during at least one potential step; a test electrode of platinum is used; and a membrane is placed in front of the test electrode.

Other features and advantages of the present invention will become apparent from the following detailed description, and from the claims.

For a full understanding of the present invention, reference should now be made to the following detailed description and to the accompanying drawings.

DETAILED DESCRIPTION

Figure 1:
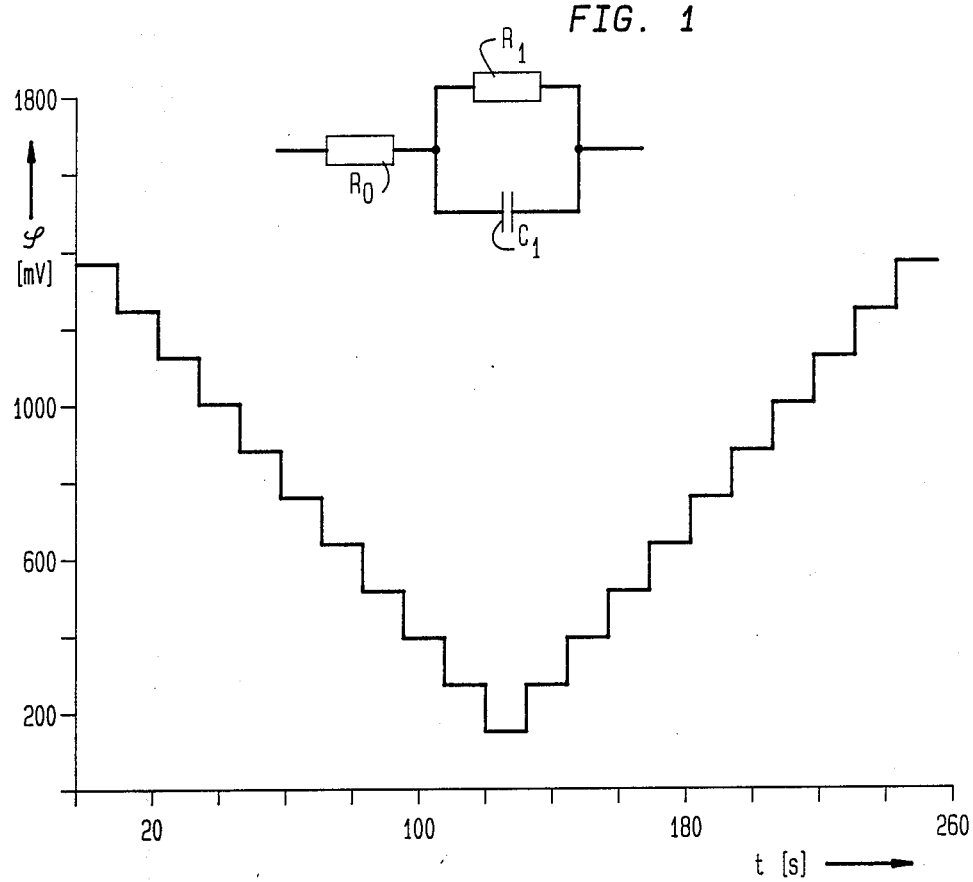
FIG. 1 shows a basic profile of the potential used in the preferred embodiment.

In the method of this invention, the potential is generally impressed on the test electrode by means of a potentiostat. The potential oscillates between two limits that are determined by the substances being examined. When the concentration of glucose, urea, and amino acids is determined, for example, the potential range lies between the potential of the reversible hydrogen electrode ($H_{2rev}$) and 1650 mV; when the concentration of oxygen or chlorine is determined, the following potential range is selected:

$$250\ mV \leq H_{2rev} \leq 1450\ mV$$

Generally, the potential interval in each case is dependent upon the substance to be evaluated, the additional substances in the solution, the type of material in the electrode, and, if applicable, the membrane in front of the test electrode.

The basic profile of the potential consists of a number of steps with the intervals between these potential steps being the same or variable. An ac voltage with a predefined amplitude and frequency is superimposed on the basic profile. In this case, the amplitude of the potential must be small in comparison with the interval width. The preferable amplitude is 10 mV, but it can be as high as 100 mV, for example. The frequency is predefined by the double-layer capacity of the electrode and, if applicable, by the resistance of the membrane. However, the highest usable frequency is 10 kHz. The lower limit of the frequency is determined by the permissible duration of the cycles.

In the method of this invention, the real and imaginary portions of the electrode impedance are determined for the individual potential steps. Both portions are influenced by the concentration of the substances present in the solution. In addition, they are influenced by the potential. If a calibration is performed, and the impedance is determined as a function of the various potentials at a fixed amplitude and frequency, the coefficients of an evaluation pattern are obtained. The concentration of the substance to be determined can then be derived from this evaluation method.

An essential point of this invention is that no increased demands be placed on the catalytic activity of the test electrode. However, a prerequisite for this is that the reactants are converted on the electrode. Preferably, a platinum electrode is used for this method. In addition, it is also advantageous if a membrane is placed in front of the test electrode. This membrane then protects the electrode from large molecules such as protein substances, which can cause interference and thus prevent a conversion. The membrane can also be used as a diffusion boundary for the substances diffusing through it; thus bringing about a preselection of smaller molecules.

The preferred thickness (c) of the hydrophilic membrane placed in front of the test electrode is less than 50 microns. Moreover, diffusion coefficients (D) of the membrane must be as small as possible; the objective being $D<10^{-8}$ cm$^2$/sec. Synthetic substances which form relatively hydrophobic foils can be used to manufacture such a membrane. These synthetic substances are then made hydrophilic using conventional procedures.

The method of this invention makes it possible to analyze the substances that react electro-chemically or are absorbed by the test electrode. By means of this procedure, several individual electrochemically active components can be determined concurrently.

It is therefore possible, for example, to determine the concentration of glucose even in the presence of urea and amino acids.

If, for example, only the capacity of the test electrode is used for the evaluation during the determination of the glucose concentration ($\gamma=1$ Hz), a measurement error of approximately 20% results if the potential interval is divided into eleven equidistant potential steps and if these potential steps are given equal priority in evaluation. If, on the other hand, the steps selected for the evaluation are the ones which exhibit the most pronounced changes in impedance when the concentration varies, and if both the real and the imaginary portions of the impedance are taken into consideration, the measurement error can be reduced to less than 10%.

The invention will now be explained in greater detail with reference to specific embodiments and to the figures.

When the concentration is to be determined according to this invention, an electro-chemical sensor is used which has an analyzer consisting of, for example, polymethylmethacrylate. The analyzer contains a test or work electrode (AE) made of platinum (active surface: approximately 0.1 cm$^2$, for example) with a membrane, in some cases, placed in front of it. The membrane consists of, for example, polytetrafluorethylene which is grafted using quaternized benzylamine. The membrane can also consist of sulfonated polysulfone. A counter-electrode (GE) is located on the other side of the membrane in the form of a platinized platinum plate, for example.

Finally, the analyzer through which the solution containing the substances to be determined is passed in a closed circuit, is connected to a reference electrode (BE) in the form of a Hg/HgCl$_2$- electrode, for example. With reference to the membrane, the reference electrode can be placed on the side of the counter-electrode or on the side of the test electrode. In the latter case, the reference electrode is prevented from being impaired by impurities in the solution or by components of the body fluid. The use of a high-capacitive counter-electrode which is used simultaneously as a reference electrode is an advantageous method of preventing the reference electrode from being impaired.

For the impedance method, which is the abbreviated term also used for the method of this invention, it is advantageous for evaluating the results if an equivalent circuit is allocated to the electro-chemical analyzer, i.e. to the arrangement consisting of the test electrode and the membrane. The electrical quantities of this equivalent circuit can then be recorded with appropriate measurement techniques. The equivalent circuit has a resistor $R_1$ and a capacitor with capacitance $C_1$ connected in parallel. This R/C network is connected in series to an additional resistor $R_0$ (see FIG. 1). The equivalent circuit changes as a function of the potential on the test electrode and as a function of the concentration; e.g., the glucose concentration. However, only the electric quantities change and not their arrangement.

The configuration of the equivalent circuit can be derived directly from the "Nyquist plot". The "Nyquist plot" (in the shape of a semi-circle) represents the imaginary portion of the impedance versus the real portion (it should be noted that impedance is understood to mean the apparent resistance in ac circuits). The numerical value of the impedance is derived from the quotient $U_{eff}/I_{eff}$. The following applies to a purely sinusoidal voltage:

$$U = U_0 \sin(wt + \theta) \text{ and } U_{eff} = U_0 \cdot \sqrt{2}/2$$

where w=angular frequency ($2\pi\gamma$), $\theta$=phase shift (between voltage and current) and $U_0$=amplitude (this applies correspondingly to the current I).

The real portion of the impedance is defined as $$a = \frac{U_{eff}}{I_{eff}} \cdot \cos(\tau),$$

the imaginary portion is $$b = \frac{U_{eff}}{I_{eff}} \cdot \sin(\tau)$$

If the impedance is recorded as a function of the frequency and is then represented in the form of the "Nyquist plot", information concerning the arrangement of the electrical quantities (resistors and capacitors) is obtained from the "Nyquist plot", and the electrical values of the elements of the equivalent circuit are obtained from the numerical values. The following applies to the equivalent circuit diagram described above:

at high frequency: $R_0 = a$;
at low frequency: $R_1 = a$;
at medium frequency: $C_1 = 1/wb$ If the impedance is measured periodically as a function of the frequency for each potential step of a potential staircase, which is produced when ac current is superimposed on delta voltage curves (see FIG. 1), the respective resistance and capacitance values of the electrical quantities of the equivalent are obtained for the individual steps. Measuring the impedance for many frequencies will not be necessary if a selection of the two most suitable individual frequencies in the "Nyquist plot" is made. Geometrically, this means that the semicircle can be well plotted if two points on the circumference that have a sufficient distance from each other, are known.

If the capacitance or the resistance of the individual potential steps is plotted versus the concentration, a straight line is obtained for specific potential steps. This means that the concentration is a linear function of the electrical quantity. If various substances are present in the solution being examined, and if these substances make themselves conspicuous at different potentials, which is generally the case, it is also possible to determine the concentration of all substances simultaneously.

Figure 2:
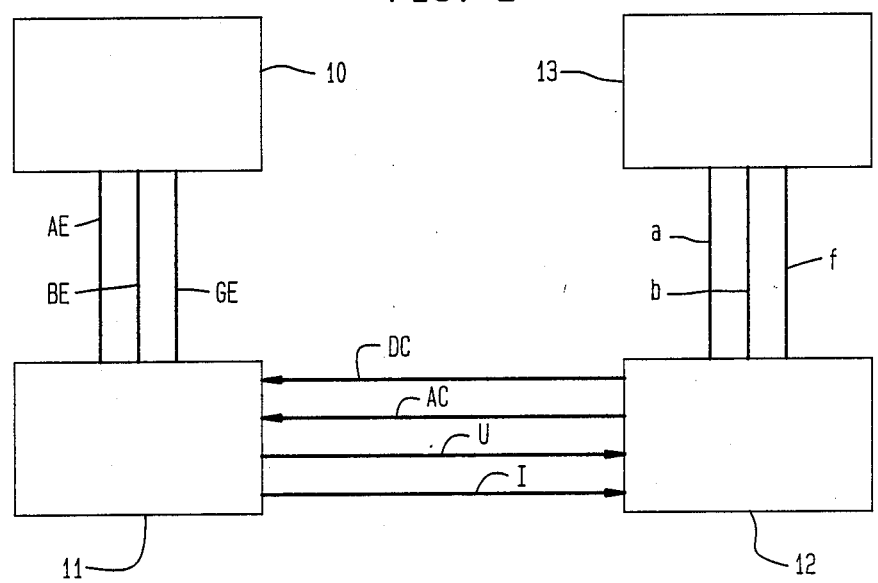
FIG. 2 shows diagrammatically, the preferred embodiment of the invention.

A potentiostat, for example, is used to determine the electrical quantities of the test electrode (with a membrane placed in front of it). The direct current voltage (dc) changing with time and the sinusoidal alternating current voltage (ac) to be overlayed are applied to the input of potentiostat 11, as shown in FIG. 2. These two voltages can be generated in the dc source and in the oscillator of frequency response analyzer 12, respectively. The response of the electrochemical system (the analyzer 10) to the ac voltage is the voltage between the test electrode (AE) and the referece electrode (BE) measured at the y-input. The voltage at the resistor in the counter electrode circuit (GE), measured acrosss the x-input, provides information regarding current. From the input values of current and voltage the r.m.s. values of the voltage at the predefined oscillator frequency ("lock-in" principle) as well as the respective phase angle are determined. From the values for the real portion (a) and the imaginary portion (b) of the impedance and for the frequency (f), the concentration is then, for example, determined by a computer 13.

By using a Raney platinum electrode as a test electrode, the concentration of glucose in a tyrode solution (solution isotonic with blood) was determined in the presence of urea by performing the following series of experiments. The impedance of the test electrode, without a membrane in front of it, was measured at frequencies from 100 Hz to 0.1 Hz for one frequency each at each potential step. The potential range was between 0 and 1650 mV, measured against the reversible hydrogen electrode; each potential step was 30 mV (duration of a step: 10 to 60 seconds). These measurements showed that it is possible to determine a glucose concentration even in the presence of urea in the normal physiological range of concentration. This correspondingly applies to the presence of physiological quantities of amino acids.

The measurement time for the above experiments was approximately 30 minutes. The measurement time can be reduced to approximately 6 minutes under the following conditions:

increase the potential steps to 150 mV (at a duration of approximately 20 seconds);
frequency 1 Hz;
amplitude 14 mV;
use a membrane in front of the platinum electrode (the membrane made of grafted polytetrafluorethylene and with a thickness of 25 microns).

This second series of experiments also showed that the concentration of glucose can be determined reliably in the presence of changing quantities of urea and amino acids (within the physiological range of concentration). The measurements were taken within the potential range of 0 to 1650 mV. In these experiments, the amino acids used in each case were a combination of all physiological compounds.

In the second series of experiments described above, the electrolyte, for example, the tyrode solution, has been saturated with a mixture of $N_2/CO_2$ (95:5). If this mixture is replaced by a mixture of compressed air/-$CO_2$, which consists for example of $O_2$, $N_2$ and $CO_2$, the results show that the influence of the oxygen causes changes in the voltage curve of the a and b values. On the other hand, it is also possible to determine the oxygen content in this manner.

In certain monitoring systems, such as devices for eliminating urea (cf. DE-OS 30 40 470), the determination of the oxygen and/or chlorine content is required. This is also possible using the method of this invention. For this purpose, the real and imaginary portions of the impedance of two frequencies are measured on a platinized platinum electrode for a potential staircase upon which alternating current is superimposed (the measurements are made without using a membrane) under the following conditions:

Potential: 250 mV $\leq H_{2rev} \leq$ 1450 mV;
Potential step: 120 mV (duration: 12 seconds);
Amplitude: 14 mV; and
Frequency: 3 Hz and 1 kHz (each one for each potential step)

The evaluation of the a and b values provides the oxygen and/or chlorine concentration (duration of measurement: 5 minutes). The results of this procedure have shown that the maximum error in determining the oxygen concentration is 0.1 mg/dl within a range of 0 to 4.1 mg/dl, and the maximum error in determining the chlorine concentration is 2 mg/dl within a range of 0 to 23 mg/dl (electrolyte: buffered 1 n KCl solution).

Therefore, this invention makes it possible to determine the concentration of substances that can be electro-chemically converted on an electrode. This method of determination (based upon the many options for variation) can be adapted well to the respective system. Therefore, changing the rate of the voltage is just as possible as an additional change in the test frequency. Furthermore, the impedance at a potential can be measured in rapid succession at different frequencies. It is then possible to separate the membrane resistance from the charge transfer resistance when the appropriate frequencies are selected. By this means, a change in the ohmic resistance of the membrane occurring during the course of time can be taken into consideration during evaluation. In the method of this invention the position of the potential interval is determined by the system being examined, and it can be easily determined by cyclic investigations by potentiometric measurements. The size of the potential steps is generally determined by the interval separating the individual potentials from each other, and by the target-time for a complete measurement cycle.

There has thus been shown and described a novel method for determining the concentration of electrochemically convertible substances which fulfills all the objects and advantages sought. Many changes, modifications, variations and other uses and applications of the subject invention will, however, become apparent to those skilled in the art after considering this specification and the accompanying drawings which disclose embodiments thereof. All such changes, modifications, variations and other uses and applications which do not depart from the spirit and scope of the invention are deemed to be covered by the invention which is limited only by the claims which follow.

What is claimed is:

1. A method for determining the concentrations of glucose, urea and/or amino acids in the presence of each other in a solution by means of an electrochemical sensor comprising a membrane-covered platinum test electrode and a counter electrode, comprising:

contacting the platinum test electrode with a physiological solution which contains glucose, urea and amino acids;

impressing a potential varying with time on the platinum test electrode in potential steps within a potential interval;

superimposing AC voltage of predetermined amplitude and predetermined different frequencies on the potential during at least one potential step;

establishing the real and imaginary portions of the impedance during said at least one potential step; and determining the concentration of glucose, urea and/or amino acids from the real and imaginary portions of the impedance established during said at least one potential step.

* * * * *